US006391281B1

(12) United States Patent
Rueggeberg et al.

(10) Patent No.: US 6,391,281 B1
(45) Date of Patent: May 21, 2002

(54) FLUORESCENT AGENT FOR THE IDENTIFICATION OF TOOTH DENTIN

(75) Inventors: Fred Rueggeberg, Augusta; Don Mettenberg, Evans; John Wataha; Frank Caughman, both of Martinez; George Schuster, Augusta, all of GA (US)

(73) Assignee: Medical College of Georgia Research Institute, Augusta, GA (US)

( * ) Notice: Subject to any disclaimer, the term of this patent is extended or adjusted under 35 U.S.C. 154(b) by 0 days.

(21) Appl. No.: 09/573,923

(22) Filed: May 18, 2000

(51) Int. Cl.[7] ............................ A61B 10/00; A61B 5/00; A61B 8/00; A01N 43/16; A61K 31/35
(52) U.S. Cl. ......................... 424/9.6; 424/9.7; 514/453
(58) Field of Search ............................. 424/1.65, 9.1, 424/9.6, 9.7; 514/680, 688, 689, 724, 721, 732, 453

(56) References Cited

U.S. PATENT DOCUMENTS

| | | | |
|---|---|---|---|
| 3,574,943 A | | 4/1971 | Stark et al. |
| 3,903,252 A | | 9/1975 | Stearns et al. |
| 4,146,606 A | | 3/1979 | Yamaga et al. |
| 4,517,172 A | | 5/1985 | Southard |
| 4,748,198 A | | 5/1988 | Takahashi et al. |
| 4,875,858 A | | 10/1989 | Jefferies et al. |
| 5,023,107 A | | 6/1991 | Roberts |
| 5,100,649 A | * | 3/1992 | Caslavsky et al. ............ 424/52 |
| 5,102,461 A | | 4/1992 | Rheinberger et al. |
| 5,269,682 A | | 12/1993 | Kesling |
| 5,876,208 A | * | 3/1999 | Mitra et al. ............... 433/217.1 |
| 6,048,545 A | * | 4/2000 | Keller et al. ................. 424/450 |
| 6,135,774 A | * | 10/2000 | Hack et al. .................. 433/215 |
| 6,187,838 B1 | * | 2/2001 | Dickens et al. ............. 523/118 |

FOREIGN PATENT DOCUMENTS

| | | |
|---|---|---|
| JP | 60089752 A | 5/1985 |
| JP | 11-58086 | 6/1989 |

OTHER PUBLICATIONS

Whitehead et al. "Removal of Porcelain Veneers Aided by a Fluorescing Luting Cement", Journal of Esthetic Dentistry, 12:30–45, Jan. 2000.*

Ekert et al. "Effect of Two Fluorescent Dyes on Color of Restorative Materials", American Journal of Dentistry, 10 (4), Aug. 1997.*

Yoshida et al. "Identification of Artificial Teeth by Fluorescent Examination wiht an Emphasis on Metal Bond Porcelaine", Japanese Journal of Legal Medicine, 47 (4) 310–4, Aug. 1993.*

Van der Veen, et al. "Evaluation of Sodium Fluorescein for Quantitative Diagnosis of Root Caries," J. Dental Research, 17(10) 1487–9 (1996).*

Patel, et al., "Determining Periodontal Ligament Cell Vitality from Exarticulated Teeth Stored in Saline or Milk Using Fluorescein Diacetate", International Endodontic J., 27(1) 1–5, (Jan. 1994).*

Fujisawa, et al., "Preferential Adsorption of Dentin and Bone Acidic Proteins on the Face of Hydroxyapatite Crystals", Biochim. Biophy. Acta, 1075(1) 56–60 (1991).*

VAn Dijk, et al., "Surface–free Energy and Bacterial Adhesion. An in vivo Study in Beagle Dogs", J. of Clinical Peridontology, 14(5) 300–4 (1987).*

Schupbach, et al., "Dentin Bonding: Effect of Tubule Orientation on Hybrid Layer Formation", J. Oral Sciences, 105(4) 344–52 (1997).

Griffiths, et al., "The Influence of Dentine Bonding Systems and Their Handling Characteristics on the Morphology and MIcropermeability of the Dentine Adhesive Interface", J. Dentistry, 27(1) 63–71 (1999).

Van der Veen, et al., "A fiber Optic Setup for Quantification of Root Surface Demineralization", 104(2(Pt 1)) 118–22 (1996).

Byers, et al. "Odontoblast Processes in Dentin Revealed by Fluorescent Di–I," J. Biochem. and Cytochem., 43(2)159–168 (1995).

Van Der Veen et al., "An in vitro evaluation of fluorescein penetration into natural root surface carious lesions,"*Caries Research*, 27(4)258–261 (1993) (Abstract).

* cited by examiner

*Primary Examiner*—Dameron L. Jones
*Assistant Examiner*—Lauren Q. Wells
(74) *Attorney, Agent, or Firm*—Needle & Rosenberg, P.C.

(57) ABSTRACT

A method of topically applying a fluorescing agent to a cut tooth, cut dental restorative material or dentin surface to distinguish between cut tooth or dentin and existing aesthetic restoration material or enamel specifically for the purposes of detection and identification of the tooth tissue dentin.

16 Claims, 6 Drawing Sheets

Figure 1
Absorbance Spectrum of Camphorquinone

Figure 2
Absorbance Spectrum of Bandpass Filter

Figure 4
Spectral Excitation and Emission of Fluoroscein

Figure 5
Absence of Fluorescence of Dentin without Fluorescein Application, Irradiation with a Blue Output Curing Light, and Visualizing Through "Blue Blocker" Filters Figure 6
Fluorescence of Dentin Following Fluorescein Application, Irradiation with a Blue Output Curing Light, and Visualizing Through "Blue Blocker" Filters

FLUORESCENT AGENT FOR THE IDENTIFICATION OF TOOTH DENTIN

FIELD OF THE INVENTION

This invention relates generally to a novel method of enhancing the visual or instrumental identification of dentin, or tooth tissue, by applying a fluorescing agent to a cut tooth, cut dental restorative material or dentin surface.

BACKGROUND OF THE INVENTION

The use of aesthetic (tooth colored) restorative materials in the practice of dentistry has grown tremendously in recent years. The products comprising this type of restoration include porcelain, resin- and ionomer-based materials. Human teeth have a natural fluorescence and manufacturers have purposefully added fluorescing agents to restorative materials so that the restorations will not be distinguishable from the natural conditions upon exposure to black light, ultraviolet energy (UV).

A problem facing the restorative dentist is the complete removal of existing aesthetic-based restorative materials during their replacement due to restoration failure or some other reason. The difficulty in this task is the identification of the point at which old, aesthetic restorative material has been completely removed, and fresh tooth structure has been exposed. The profession has decided to eliminate the use of introral ultraviolet radiation. Previously, UV radiation was specifically used to cause the photo-polymerization of the first generation of radiant-polymerized, direct-placed dental restorative materials. Potential eye problems resulting from low dosages of UV radiation over a long-term to both the clinician and staff as well as the possibility of inducing mutations in the patient's oral microflora resulted in the use of energy only within the visible spectrum. Thus, energy associated with the visible spectrum is now used to supply the radiation necessary to cause radiant cure of resin-based, aesthetic restorative materials. Current technology utilizes a photo-active agent (typically camphorquinone (CQ)), which has its absorbance maximum between 400 and 500 nm blue light, to provide free radicals necessary for introral polymerization. The spectral absorbance of CQ is provided in FIG. 1.

In order to accommodate for the specific needs of a blue light photoinitiator, the curing light output is filtered to eliminate heat-causing infrared energy, and to limit the bandpass region of visible light between 400 and 500 nm. The absorbance profile of a typical bandpass filter of a dental light curing unit is seen in FIG. 2.

Figure 1:
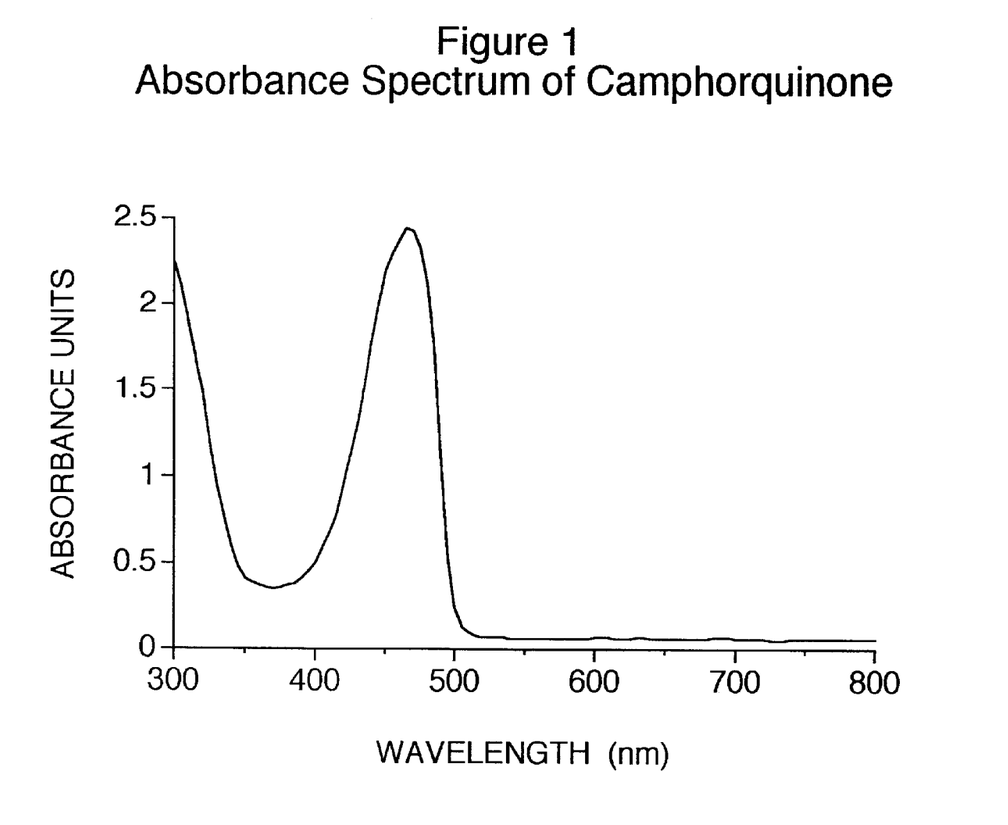
FIG. 1 shows the spectral absorbance for a photoactive agent, camphorquinone, typically used for blue light curing of dental restorative materials.
Figure 2:
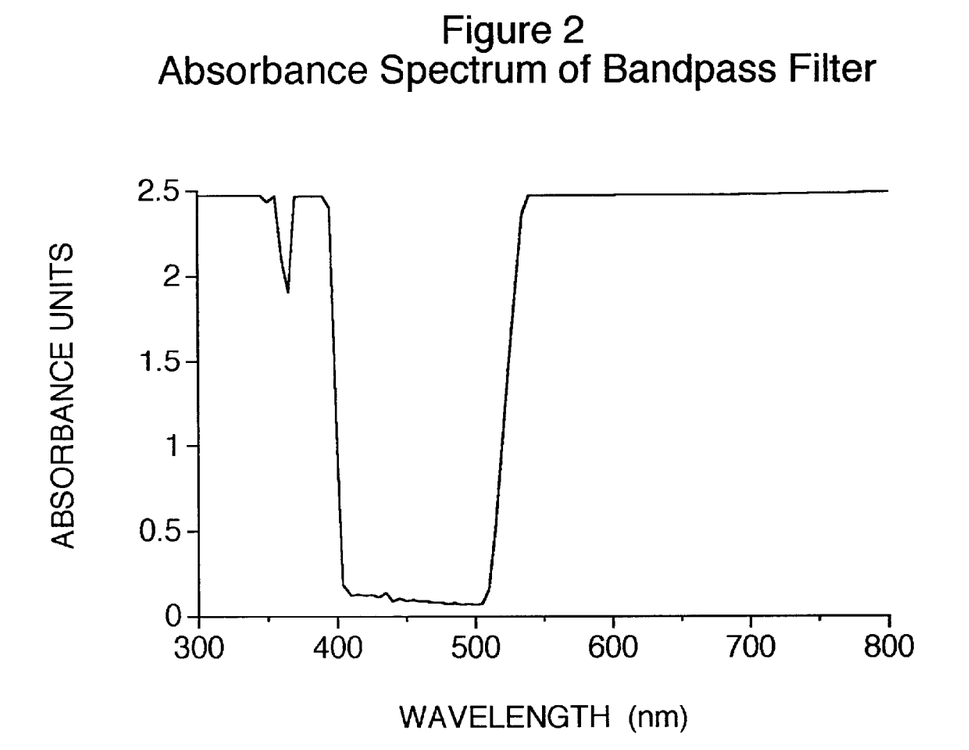
FIG. 2 shows the absorbance profile of a typical visible bandpass filter of a dental light-curing unit.
Figure 3:
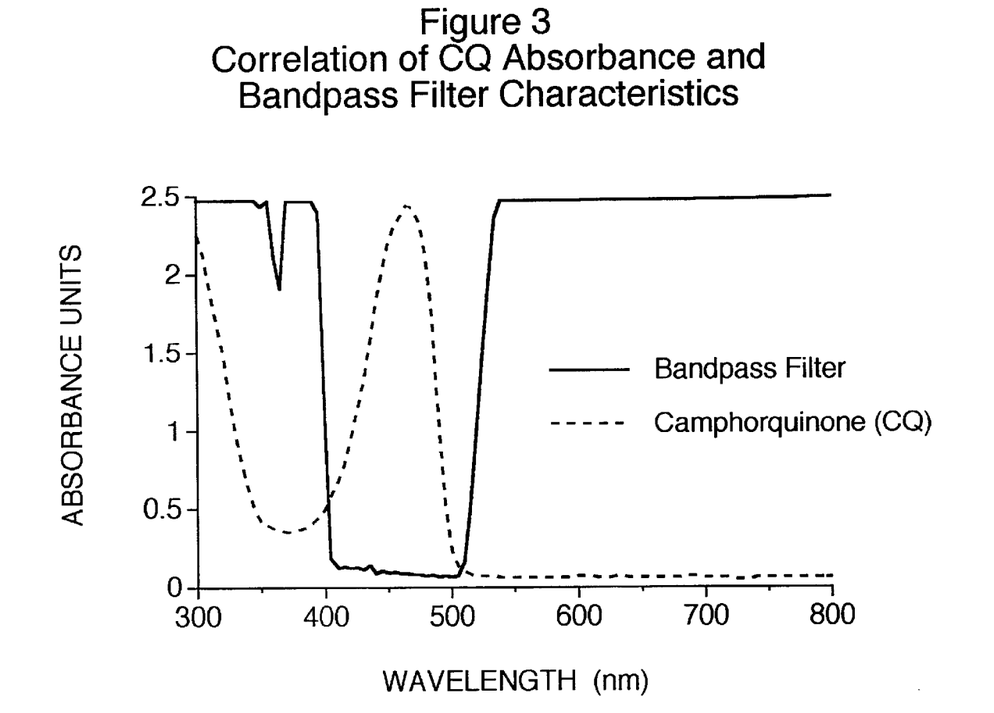
FIG. 3 superimposes FIGS. 1 and 2 and provides an indication of the restriction of energy emitted from a typical dental photo-curing unit and its relationship to the absorption spectrum of camphorquinone.

Overlying FIGS. 1 and 2 provides an indication of the restriction of energy emitted from a typical dental photo-curing unit and its relationship to the absorption spectrum of a typical photoinitiator, CQ (FIG. 3).

U.S. Pat. No. 5,102,461 (hereinafter '461) teaches adding a fluorescent agent to a dental material composition, such that upon application of radiant energy of an appropriate wavelength, the fluorescent agent in the dental material emits fluorescence, which permits visual distinction of the material from the tooth structure.

U.S. Pat. No. 5,269,682 (hereinafter '682) teaches a method of identifying and removing orthodontic bonding adhesive utilizing a fluorescing agent in the bonding agent composition which attaches an orthodontic bracket to the enamel surface of a tooth. Upon removal of the bracket, distinction between the enamel and unremoved bonding resin is aided by the use of the fluorescein in the bonding agent.

The fluorescent agent in this invention is different from '461, in that '461 does not disclose fluorescein fluorescing agents and incorporates the fluorescent agent into a dental material. Furthermore, it is not intended that the fluorescing agent herein is added to a bonding composition as in '682, but is mixed with a transferring agent and applied directly to cut tooth or dentin to aid in distinguishing between cut tooth or dentin and enamel during the removal of existing aesthetic based restorative materials.

SUMMARY OF THE INVENTION

The above-mentioned problem of completely removing existing aesthetic-based restorative material is overcome by providing a fluorescing agent which will aid in visually or instrumentally detecting the presence of dentin.

In one embodiment, the invention provides a method of topically applying a fluorescing agent to a cut tooth or restoration surface having an existing aesthetic restoration comprising the steps of:

a) topically applying a composition consisting essentially of a fluorescing agent to a cut tooth or restoration surface in an effective amount to provide adequate detection of emitted radiation;

b) irradiating the cut tooth or restoration surface with a light source emitting a wavelength in the visible spectrum of about 380 to about 700 nm; and c) visually or instrumentally identifying the fluorescing agent by observing emitted fluorescence at a wavelength of lower energy than the excitation energy to distinguish between dentin and existing restoration material and/or enamel on the cut tooth or restoration surface, wherein the fluorescing agent bonds/binds to dentin in preference to enamel or to the aesthetic restoration material.

In another embodiment, the invention provides a method of topically applying a fluorescing agent to a cut tooth surface free of existing aesthetic restoration comprising the steps of:

a) topically applying a composition consisting essentially of a fluorescing agent to a cut tooth surface in an effective amount to provide adequate detection of emitted radiation;

b) irradiating the cut tooth surface with a light source emitting a wavelength in the visible spectrum of about 380 to about 700 nm; and c) visually or instrumentally identifying the fluorescing agent by observing emitted fluorescence, at a wavelength of lower energy than the excitation energy to distinguish between dentin and enamel on the cut tooth surface, wherein the fluorescing agent bonds/binds to dentin in preference to enamel.

In another embodiment, the invention provides a method of topically applying a fluorescing agent to a cut tooth or restoration surface of an existing aesthetic restoration comprising the steps of:

a) topically applying a fluorescing material consisting essentially of phosphate buffered to pH 7 saline solution of fluorescein sodium salt to a cut tooth or restoration surface in an effective amount to provide adequate detection of emitted radiation;

b) irradiating the cut tooth or restoration surface with a light source emitting a wavelength in the visible spectrum of about 380 to about 700 nm; and c) visually or instrumentally identifying the fluorescing agent by observing emitted fluorescence at a wavelength of lower energy than the excitation energy to distinguish between dentin and existing aesthetic restoration material and/or enamel on the cut tooth or restoration surface, wherein the topically applied fuorescein sodium salt solution bonds or binds to the dentin in preference to enamel or to the aesthetic restoration material.

In another embodiment, the invention provides a method of topically applying a fluorescing agent to a cut tooth surface free of existing aesthetic restoration comprising the steps of:

a) topically applying a fluorescing material consisting essentially of phosphate buffered to pH7 saline solution of fluorescein sodium salt to a cut tooth surface in an effective amount to provide adequate detection of emitted radiation;

b) irradiating the cut tooth surface with a light source emitting a wavelength in the visible spectrum of about 380 to about 700 nm; and c) visually or instrumentally identifying the fluorescing agent by observing emitted fluorescence at a wavelength of lower energy than the excitation energy to distinguish between dentin and/or enamel on the cut tooth surface, wherein the fluorescing agent bonds or binds to dentin in preference to enamel.

In another embodiment, the invention provides a topical composition for applying to a cut tooth or restoration surface consisting essentially of a fluorescing agent and a transferring agent.

In another embodiment, the invention provides a topical composition for applying to a cut tooth or restoration surface consisting essentially of a sodium salt of fluorescein and a phosphate buffered saline buffered to pH 7.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

The accompanying drawings which are incorporated in and constitute a part of this specification, illustrate several embodiments of the invention and together with the description, serve to explain the principles of the invention.

DETAILED DESCRIPTION OF THE INVENTION

The present invention may be understood more readily by reference to the following detailed description of the invention and the examples included herein.

This invention relates to the use of a fluorescing agent which is applied to a tooth surface for the specific purpose of visually identifying the presence of the specific tooth tissue, dentin. Such a distinction is important in identifying the difference between remaining restorative material and cut tooth tissue (specifically dentin). Also, detection of exposed dentin may be of importance when agents must be applied to enhance bonding techniques or to protect underlying tooth tissue (placement of veneers and indirect pulp capping). This distinction is of paramount importance when existing aesthetic (tooth colored) restorative material must be removed and replaced as a result of recurrent decay or some other process. Also, when teeth are prepared for veneers, the areas of exposed dentin are important to identify because they will be treated differently than exposed enamel. The unique features of this invention are that the fluorescing agent binds or bonds specifically to the internal tooth tissue (dentin) and not to the outer tissue (enamel) or to the restorative material. The energy of excitation of the fluorescing agent is typically within the visible light spectrum, and the energy of emission is of a lower wavelength, but of an energy level sufficient to provide facile visual or instrumental distinction from the excitation color.

In order to utilize a fluorescing agent which is compatible with contemporary dental photocuring units as the source of excitation, the fluorescing agent must have an absorption maximum within the bandpass of the curing light filter, and an emission energy lower in wavelength than the light emanating from the light source. There are many fluorescing agents which will meet these requirements, and which are disclosed herein.

It must be noted that, as used in the specification and the appended claims, the singular forms "a," "an" and "the" include plural referents unless the context clearly dictates otherwise.

Ranges are often expressed herein as from "about" one particular value, and/or to "about" another particular value. When such a range is expressed, another embodiment includes from the one particular value and/or to the other particular value.

A weight percent of a component, unless specifically stated to the contrary, is based on the total weight of the formulation or composition in which the component is included.

The terms "tooth tissue" and "dentin" are synonymous and are meant to describe the hard portion of the tooth surrounding the pulp, covered by enamel on the crown and cementum on the root, which is harder and denser than bone but softer than enamel.

The term "cut tooth" is meant to describe the area of the tooth which is cut for a cavity preparation and may comprise restorative material (in the case of an existing restoration), an enamel area and a dentin area.

By the term "effective amount" of a compound or property as provided herein is meant such amount as is capable of performing the function of the compound or property for which an effective amount is expressed. As will be pointed out below, the exact amount required will vary from process to process, depending on recognized variables such as the compounds employed and the processing conditions observed. Thus, it is not possible to specify an exact "effective amount." However, an appropriate effective amount may be determined by one of ordinary skill in the art using only routine experimentation.

The term "transferring agent" refers to the carrier which is mixed with the fluorescing agent.

In one embodiment, the invention provides a method of topically applying a fluorescing agent to a cut tooth or restoration surface having an existing aesthetic restoration comprising the steps of:
a) topically applying a composition consisting essentially of a fluorescing agent to a cut tooth or restoration surface in an effective amount to provide adequate detection of emitted radiation;
b) irradiating the cut tooth or restoration surface with a light source emitting a wavelength in the visible spectrum of about 380 to about 700 nm; and
c) visually or instrumentally identifying the fluorescing agent by observing emitted fluorescence at a wavelength of lower energy than the excitation energy to distinguish between dentin and existing aesthetic restoration material and/or enamel on the cut tooth or restoration surface, wherein the fluorescing agent binds to dentin in preference to enamel or to the aesthetic restoration material.

In another embodiment, the invention provides a method of topically applying a flurorescing agent to a cut tooth surface free of existing aesthetic restoration comprising the steps of:
a) topically applying a composition consisting essentially of a fluorescing agent to a cut tooth surface in an effective amount to provide adequate detection of emitted radiation;
b) irradiating the cut tooth surface with a light source emitting a wavelength in the visible spectrum of about 380 to about 700 nm; and
c) visually or instrumentally identifying the fluorescing agent by observing emitted fluorescence at a wavelength of lower energy than the excitation energy to distinguish between dentin and enamel on the cut tooth surface, wherein the fluorescing agent binds to dentin in preference to enamel.

In another embodiment, the invention provides a method of topically applying a fluorescing agent to a cut tooth or restoration surface of an existing aesthetic restoration comprising the steps of:
a) topically applying a fluorescing material consisting essentially of phosphate buffered to pH 7 saline solution of fluorescein sodium salt to a cut tooth or restoration surface in an effective amount to provide adequate detection of emitted radiation;
b) irradiating the cut tooth or restoration surface with a light source emitting a wavelength in the visible spectrum of about 380 to about 700 nm; and
c) visually or instrumentally identifying the fluorescing agent by observing emitted fluorescence at a wavelength of lower energy than the excitation energy to distinguish between dentin and existing aesthetic restoration material and/or enamel on the cut tooth or restoration surface, wherein the topically applied fluorescein sodium salt solution bonds/binds to the dentin in preference to enamel or to the aesthetic restoration material.

In another embodiment, the invention provides a method of topically applying a fluorescing agent to a cut tooth surface free of existing aesthetic restoration comprising the steps of:
a) topically applying a fluorescing material consisting essentially of phosphate buffered to pH7 saline solution of fluorescein sodium salt to a cut tooth surface in an effective amount to provide adequate detection of emitted radiation;
b) irradiating the cut tooth surface with a light source emitting a wavelength in the visible spectrum of about 380 to about 700 nm; and
c) visually or instrumentally identifying the fluorescing agent by observing emitted fluorescence at a wavelength of lower energy than the excitation energy to distinguish between dentin and/or enamel on the cut tooth surface, wherein the fluorescing agent bonds/binds to dentin in preference to enamel.

In another embodiment, the invention provides a topical composition for applying to a cut tooth or restoration surface consisting essentially of a fluorescing agent and a transferring agent.

In another embodiment, the invention provides a topical composition for applying to a cut tooth or restoration surface consisting essentially of a sodium salt of fluorescein and a phosphate buffered saline buffered to pH 7.

In another embodiment, the invention provides a method of mixing the fluorescing agent with a transferring agent before topically applying the fluorescing agent to a tooth surface, followed by rinsing and drying.

In each of the embodiments, the fluorescing agent can be applied with a simple instrument, such as a cotton tipped applicator. The fluorescing agent is present in the range of from about 0.001 to about 10% by weight of the total composition, more preferably from about 0.001 to about 1%, and most preferably from about 0.01 to about 0.200%.

Figure 4:
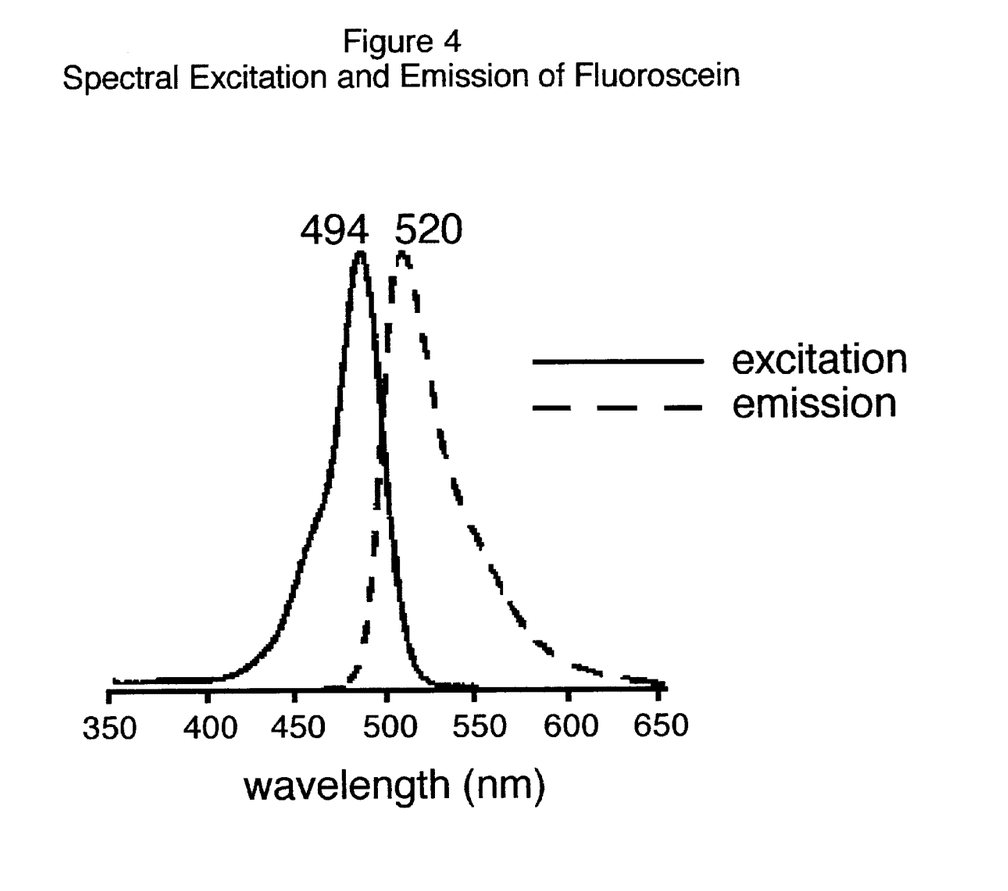
FIG. 4 shows the excitation/emission spectra of a fluorescent agent, fluorescein, utilized to demonstrate the utility of the present invention.

In one embodiment, the fluorescing agent is fluorescein. Fluorescein is a commonly used fluorescent dye in immunohistochemistry as well as in medical diagnosis. Fluorescein has the formula $C_{20}H_{12}O_5$ and the following structure:

The disodium salt (CAS registry [518-47-8], Merck Index #4085, $C_{20}H_{10}Na_2O_5$) is highly water soluble and is widely applied in tracing water flow and evaluation of plumbing leaks. Preferred fluorescing agents are fluorescein ($C_{20}H_{12}O_5$), which may be used as the disodium salt and may also be known as resorcinol phthalein sodium, uranine, uranine yellow, D&C yellow No. 8., CI Acid Yellow 73, CI 45350, AK-fluor, Fluorescite, Florets, Fluor-i-strip, Ful-go, Fundiscein, and I-rescein. Fluorescein has an absorption maximum of 494 nm and an emission of 520 nm, as seen in FIG. 4.

This excitation/emission profile is compared to the bandpass restriction utilized in dental photocuring units (FIG. 2). It can be seen that fluorescein is excited by energy emitted from the light-curing unit, and that its fluorescence will be of a wavelength other than that passed by the light-curing filter.

Fluorescein is highly biocompatible, and is frequently used topically in ophthalmic solutions for observing corneal abrasions, and intravenously for retinal angiography. It is also approved by the FDA for use in externally applied drugs and cosmetics. In histochemistry, it is used to indicate the presence of proteins, as fluorescein and its analogs bind to amino acids present in proteins.

Fluorescein is a preferred fluorescing agent because of its capability of binding to the proteinaceous structure of cut dentin. Dentin is composed of a mixture of inorganic components (hydroxyapatite, 45 volume %), organic material (mainly type II collagen, 33% volume) and water (22% volume). Also, fluorescein will not adhere to either enamel or to the components of an aesthetic-based dental restorative material (a polymer, an ionomer, or a ceramic). These later materials (enamel or aesthetic-based dental restorative material) will not bind fluorescein because they lack significant protein content.

Modification of the fluorescing agent includes the use of conjugated fluorescing agents which expand the energy range within which absorption and emission of fluorescence occurs. Such a modification would provide a fluorescing color much different from that of the illuminating source, providing easier visual detection and sensitivity of the presence of the fluorescing agent. The molecular weight of the agent can also be adjusted so that the agent does not enter and flow down dentinal tubules. Such a modification would permit only the top-most dentin surface to be detected. Removal of the fluorescing agent, if desired, would thus be facilitated with minimal abrasion of the treated dentin surface.

Additional fluorescing agents that are suitable for this invention are, for example, disclosed in U.S. Pat. No. 5,102,461, the disclosure of which is incorporated herein by reference. Included within these fluorescing agents are coumarin derivatives, phthalimide derivatives, fluoranthrene derivatives, perylene derivatives, xanthene derivatives, thioxanthene derivatives, pyrano-benzopyran-2,5-dione derivatives, pyrano-quinoline-2,5 derivatives, pyrazole quinoxlaine derivatives, 2-pyrano-isoquinoline-3,6-dione derivatives, benzimidazo-benz-isoquinoline-7-one derivatives, acridine derivatives and mixtures thereof.

The recommended uses for the fluorescing agent includes the distinction of dentin (1) when using aesthetic restorative materials, to the exclusion of ceramic or resin-based restorative materials or (2) in any case, to dental enamel.

A typical transferring agent in this invention is a phosphate buffered saline solution (pH 7). However, other transfer agents may be used provided they solubilize the fluorescing agent and prove to be compatible. Additional transferring agents include any aqueous-based agent(s), which solubilizes the fluorescent agent, to include, but not limited to tap water, distilled water, deionized water, or medical grade water. An organic transfer agent can also be used to solubilize the fluorescent agent, and includes alcohols such as methanol, ethanol, propanol or butanol, or other solvents, more specifically, chloroform or acetone. The transferring agent is present in the amount of from about 49 to about 99.9% by weight of the total composition, more preferably from about 95 to about 99.9% by weight of the total composition, and most preferably from about 99.0 to about 99.99% by weight of the total composition.

In this invention, the steps of irradiating the cut tooth or restoration surface and visually or instrumentally identifying the fluorescing agent follow the step of topically applying the fluorescing agent to a cut tooth or restoration surface. After topical application of the fluorescing agent to the cut tooth or restoration surface, the cut tooth or restoration surface is irradiated with a light source emitting a wavelength in the visible spectrum of about 380 to 700 nm. The energy of excitation of the fluorescing agent is typically within the visible light spectrum, and the energy of emission is of a lower wavelength; but of an energy level sufficient to provide facile visual or instrumental distinction from the excitation color. As a result of the fluorescing agent's unique ability to bond specifically to tooth tissue, rather than enamel, the practitioner is visually or instrumentally aided in identifying the presence of dentin in preference to aesthetic restorative material or enamel. Visual enhancement of fluorescence may be possible by the operator viewing the irradiated area while using a visual bandpass filter which would attenuate the irradiation emitted by the irradiating source while passing energy associated with the emission frequencies of the fluorescing agent.

Experimental

The following examples are put forth so as to provide those of ordinary skill in the art with a complete disclosure and description of how the compounds claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight.

EXAMPLE 1

Test for Utility and Selectivity of the Fluorescent Agent

A freshly extracted bovine lower incisor was obtained and a cavity preparation was made into the facial surface through the enamel and 1 mm into the dentin. The preparation was then filled using a commercially available, photo-activated resin composite system sold by Kerr/Sybron Corporation in Glendora, Calif., under the trade name OPTIBOND/ HERCULITE XRV. This system consists of the use of an acid etchant, a dentin primer, dentin adhesive, and a filled resin composite system which was subsequently photocured using a conventional dental light-curing source (Optilux 501), manufactured by Demetron Corporation in Danbury, Conn.

Subsequent to the restoration placement, the tooth was ground mesio-distally from the incisal edge such that a cross-section was created which transected the tooth through the restoration, exposing the inner restorative surface as well as the dentin. The tooth was then illuminated utilizing the dental photocuring unit previously mentioned, while filtering the image through commercially available orange-colored glasses ("blue blockers") (Item #100-4634), Protective Glasses, Henry Schein Inc., Port Washington, N.Y. Use of these glasses greatly enhances the operator's ability to visualize fluorescein fluorescence because they permit passage of radiation greater than 500 nm in wavelength. The resulting image is seen in FIG. 5.

A cotton-tipped applicator was then immersed into a 1 mg/mL phosphate buffered saline solution (pH 7) of fluorescein sodium salt (item #F-6377), which is commercially available from Sigma Chemical Company, St. Louis, Mo., and wiped across the sectioned area, making sure to contact the transected enamel, restorative material, and exposed dentin. The tooth was then rinsed in running water, blotted dry, and reimaged under the same lighting conditions stated above. An example of this image is seen in FIG. 6.

Figure 5:
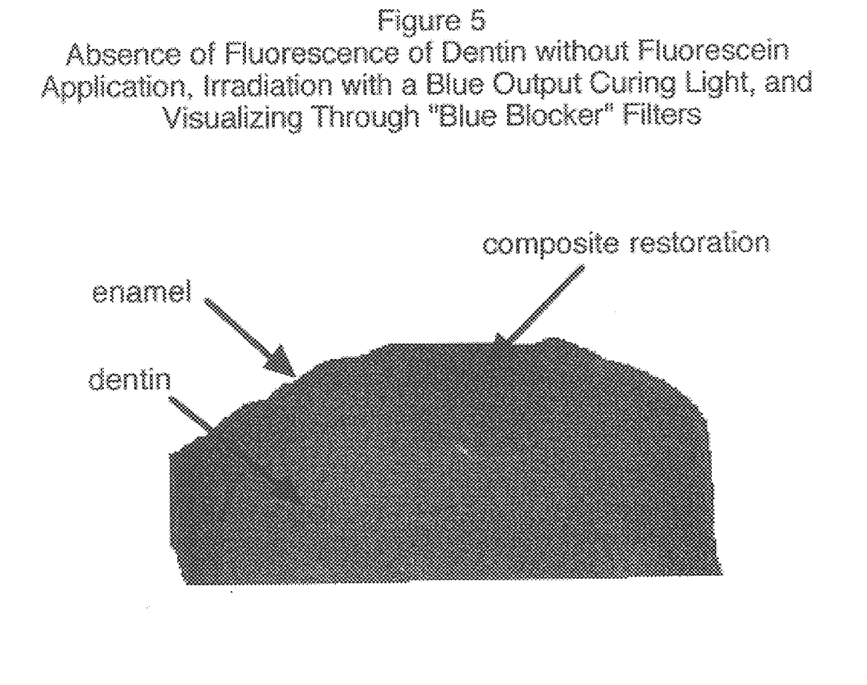
FIG. 5 shows the cross-section image of a bovine tooth containing facially placed aesthetic restoration (resin composite), showing exposed dentin and enamel.
Figure 6:
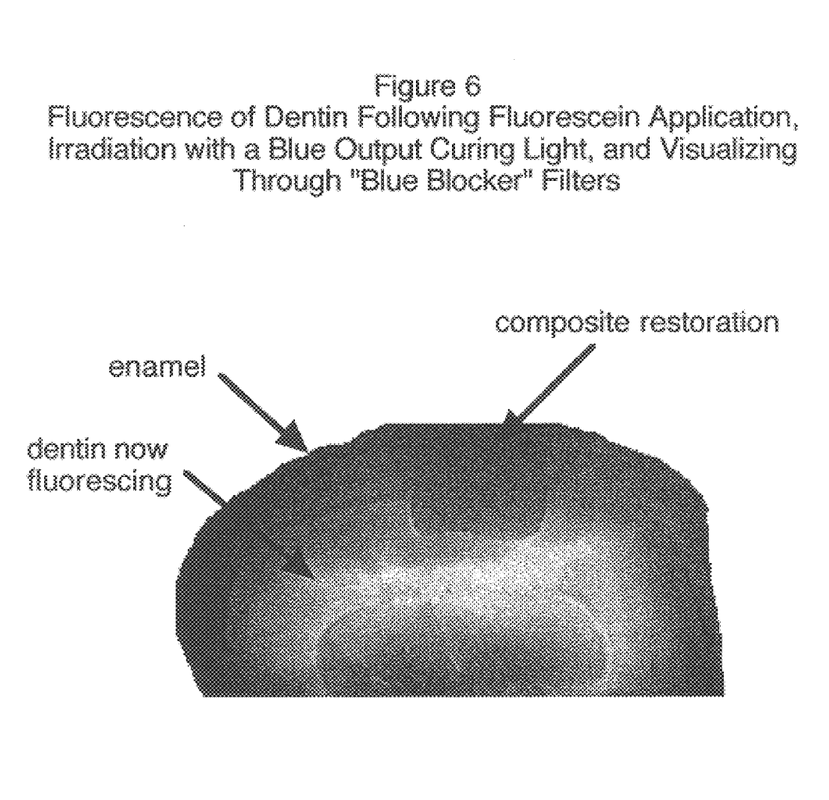
FIG. 6 shows the image of tooth cross-section demonstrating high emission of light energy within the dentin surface, and exclusion of fluorescence of the restorative material and enamel.

From the images in FIGS. 5 and 6, the identification of the tissue dentin is readily identifiable and distinguishable from the enamel and restoration when the fluorescing agent has been applied.

EXAMPLE 2
Effect of Fluorescent Agent on the Bond Strength of Resin-Based Restorative Material Because the fluorescent agent might not be completely removed from the tooth surface following its application, it is necessary to prove that its presence will not interfere with placement and bonding of an additional restoration to the treated tooth surface. To this end, a test was made to investigate this possible effect.

A total of fourteen freshly extracted lower anterior bovine incisors were obtained. The facial surface of each tooth was ground flat to remove enamel and expose dentin. The teeth were then divided equally into two groups of 7. One group served as a control and the other served as the test group which had the cut dentin surface treated with an aqueous solution of fluorescein (1 mg/mL) applied using a cotton tip applicator prior to the restorative treatment. The test tooth surface was then rinsed with water for 5 seconds, and lightly air-dried using oil-free compressed air.

All teeth were then restored using a 15-second application of acid etchant, followed by a 15-second water rinse, followed by a 5-second air drying. A dentin primer (OPTIBOND bottle 1) was then applied for 30 seconds, dried for 5 seconds with compressed air, after which a uniform, thin layer of dentin adhesive (OPTIBOND bottle 2) was applied. This layer was then subsequently light-cured for 30 seconds using a conventional dental photo-curing unit (Optilux 501). A small amount of photo-curable composite (HERCULITE XRV) was then placed on the back surface of an orthodontic bracket. The bracket was then pressed onto the prepared tooth surface and excess material around the bracket periphery was removed using a scalpel blade. The composite was then light cured from opposite sides of the bracket using 20 second exposures on each sides. The assembly was then stored in a humidor at 37° C. for 24 hours prior to shear-bond strength testing.

The strength of the bond was tested by shearing the brackets from the tooth surface using a universal testing machine (model TTB, Instron Corporation, Canton, Mass.). The cross-head speed used was 1.25 mm/min. The data from the load cell was recorded in digital format, and the load imposed at the moment of bracket failure from the tooth was determined. Table 1 provides the results of this study.

TABLE 1

Shear bond strength of bonded brackets to bovine dentin with or without fluorescing agent prior to the bonding process

| Treatment | Mean Load at Debond (lb.) | Standard Deviation |
| --- | --- | --- |
| Control (no agent applied) | 17.5 | 6.0 |
| Fluorescing agent applied | 18.3 | 4.6 |

Statistical analysis of the test results was performed using a 2-tailed, unpaired Student's t-test at a preset alpha of 0.05. The results of this analysis indicated no significant difference ($p=0.769$) in shear bond strength of teeth treated with the fluorescing agent compared to teeth which received no fluorescing agent. Thus, the presence of fluorescing agent on the tooth surface does not interfere with the subsequent ability to provide a satisfactory restoration.

EXAMPLE 3
Preparation of the Fluorescing Agent

A 1 mg/mL of phosphate buffered saline solution (pH 7) of fluorescein disodium salt (item #F-6377, Sigma Chemical) was prepared and judged excellent as a fluorescing dentin identification agent.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of topically applying a fluorescent agent to a cut tooth or restoration surface of an existing aesthetic restoration comprising the steps of:
    a) topically applying a composition consisting essentially of a fluorescing agent to a cut tooth or restoration surface in an effective amount to provide detection of emitted radiation;
    b) irradiating the cut tooth or restoration surface with a light source emitting a wavelength in the visible spectrum of about 380 to about 700 nm; and
    c) visually or instrumentally identifying the fluorescing agent by observing emitted fluorescence at a wavelength of lower energy than the excitation energy to distinguish between dentin and existing aesthetic restoration material and/or enamel on the cut tooth or restoration surface, wherein the fluorescing agent bonds or binds to dentin in preference to enamel or to the aesthetic restoration material.

2. The method of claim 1 wherein the fluorescing agent comprises the sodium salt of fluorescein.

3. The method of claim 1 wherein the fluorescing agent is in a mixture with a transferring agent.

4. The method of claim 3 wherein the transferring agent comprises a phosphate buffered saline.

5. The method of claim 4 wherein the phosphate buffered saline has a pH of 7.

6. The method of claim 1 wherein the dentin surface is rinsed and dried after topically applying the fluorescing agent.

7. A method of topically applying a fluorescent agent to a cut tooth surface free of existing aesthetic restoration comprising the steps of:
    a) topically applying a composition consisting essentially of a fluorescing agent to a cut tooth surface in an effective amount to provide detection of emitted radiation;
    b) irradiating the cut tooth surface with a light source emitting a wavelength in the visible spectrum of about 380 to about 700 nm; and
    c) visually or instrumentally identifying the fluorescing agent by observing emitted fluorescence, at a wavelength of lower energy than the excitation energy to distinguish between dentin and enamel on the cut tooth surface, wherein the fluorescing agent bonds or binds to dentin in preference to enamel.

8. The method of claim 7 wherein the fluorescing agent comprises the sodium salt of fluorescein.

9. The method of claim 7 wherein the fluorescing agent is in a mixture with a transferring agent.

10. The method of claim 9 wherein the transferring agent comprises a phosphate buffered saline.

11. The method of claim 10 wherein the phosphate buffered saline has a pH of 7.

12. The method of claim 7 wherein the cut tooth surface is rinsed and dried after topically applying the fluorescent agent.

13. A method of topically applying a fluorescent agent to a cut tooth or restoration surface of an existing aesthetic restoration comprising the steps of:
   a) topically applying a fluorescing material consisting essentially of phosphate buttered saline solution, pH 7, of fluorescein sodium salt to a cut tooth or restoration surface in an effective amount to provide detection of emitted radiation;
   b) irradiating the cut tooth or restoration surface with a light source emitting a wavelength in the visible spectrum of about 380 to about 700 nm; and
   c) visually or instrumentally identifying the fluorescing agent by observing emitted fluorescence at a wavelength of lower energy than the excitation energy to distinguish between dentin and existing aesthetic restoration material and/or enamel on the cut tooth or restoration surface, wherein the topically applied fluorescein sodium salt solution bonds or binds to the dentin in preference to enamel or to the aesthetic restoration material.

14. The method of claim 13 wherein the cut tooth or restoration surface is rinsed and dried after topically applying the fluorescein sodium salt solution.

15. A method of topically applying a fluorescing agent to a cut tooth surface free of existing aesthetic restoration comprising the steps of:
   a) topically applying a fluorescing material consisting essentially of phosphate buffered saline solution, pH7, of fluorescein sodium salt to a cut tooth surface in an effective amount to provide detection of emitted radiation;
   b) irradiating the cut tooth surface with a light source emitting a wavelength in the visible spectrum of about 380 to about 700 nm; and
   c) visually or instrumentally identifying the fluorescing agent by observing emitted fluorescence at a wavelength of lower energy than the excitation energy to distinguish between dentin and/or enamel on the cut tooth surface, wherein the fluorescing agent bonds or binds to dentin in preference to enamel.

16. The method of claim 15 wherein the cut tooth surface is rinsed and dried after topically applying the fluorescein sodium salt solution.

\* \* \* \* \*